(12) United States Patent
Eriksson et al.

(10) Patent No.: US 10,918,855 B2
(45) Date of Patent: Feb. 16, 2021

(54) SYSTEM FOR TRANSCRANIAL STIMULATION

(71) Applicant: Sooma Oy, Helsinki (FI)

(72) Inventors: Mikael Eriksson, Helsinki (FI); Jukka Kreander, Helsinki (FI); Tuomas Neuvonen, Espoo (FI); Jani Virtanen, Söderkulla (FI)

(73) Assignee: Sooma Oy, Helsinki (FI)

( * ) Notice: Subject to any disclaimer, the term of this patent is extended or adjusted under 35 U.S.C. 154(b) by 266 days.

(21) Appl. No.: 15/843,084

(22) Filed: Dec. 15, 2017

(65) Prior Publication Data

US 2018/0361140 A1 Dec. 20, 2018

Related U.S. Application Data

(60) Provisional application No. 62/434,792, filed on Dec. 15, 2016.

(51) Int. Cl.
*A61N 1/04* (2006.01)
*A61N 1/36* (2006.01)

(52) U.S. Cl.
CPC .......... *A61N 1/0484* (2013.01); *A61N 1/0456* (2013.01); *A61N 1/0496* (2013.01); *A61N 1/36025* (2013.01)

(58) Field of Classification Search
CPC ....... A61B 5/0464; A61B 5/0006; A61B 5/11; A61B 5/14551; A61B 5/14532; A61B 5/0205; A61B 5/4836; A61B 5/04325; A61B 5/0507; A61B 5/746; A61N 1/362; A61N 1/39; A61N 1/3904; A61N 1/046; A61N 1/0484
See application file for complete search history.

(56) References Cited

U.S. PATENT DOCUMENTS

2017/0080208 A1\* 3/2017 Neuvonen ............ A61N 1/0404
2017/0143228 A1\* 5/2017 Leuthardt, Jr. ..... A61B 5/04012
2018/0289945 A1\* 10/2018 Lampo ................. A61N 1/0484

FOREIGN PATENT DOCUMENTS

WO 2015173335 A1 11/2015
WO WO-2015173335 A1 \* 11/2015 ........... A61N 1/0404

\* cited by examiner

*Primary Examiner* — Rex R Holmes
(74) *Attorney, Agent, or Firm* — Ziegler IP Law Group, LLC

(57) ABSTRACT

A system for facilitating administration of transcranial stimulation. The system includes an electrode, the electrode including a counterpart configured to be attached to a headcap, a gel cup configured to be attached to the counterpart, an electrical conductor configured to be disposed within an interior space of the gel cup, and a gel pad. The gel pad is arranged to be in contact with the electrical conductor. Further, system includes a distributor, which includes at least one inlet for an aqueous solution, as well as a plurality of outlets in a fluid communication with the at least one inlet. Further, the plurality of outlets are configured to direct the aqueous solution towards the gel pad.

20 Claims, 21 Drawing Sheets

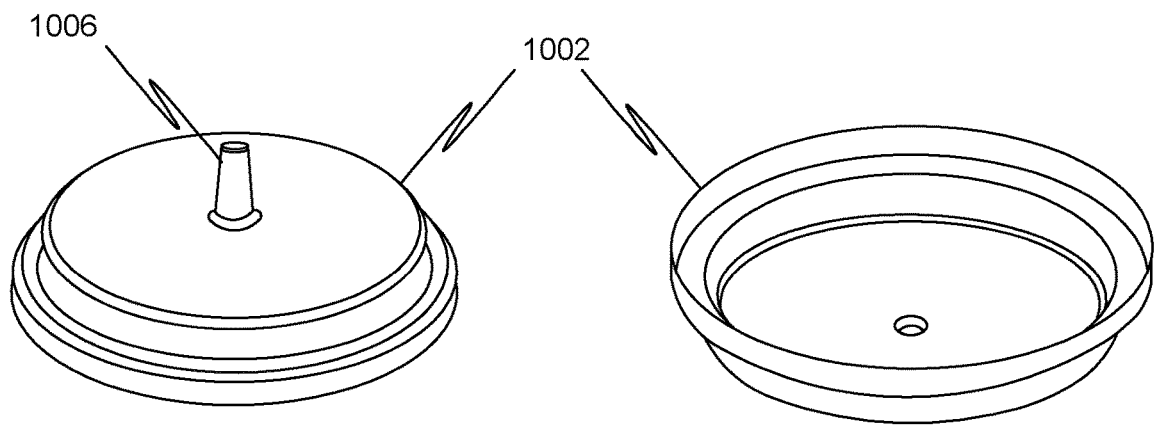
FIG. 10A  FIG. 10B
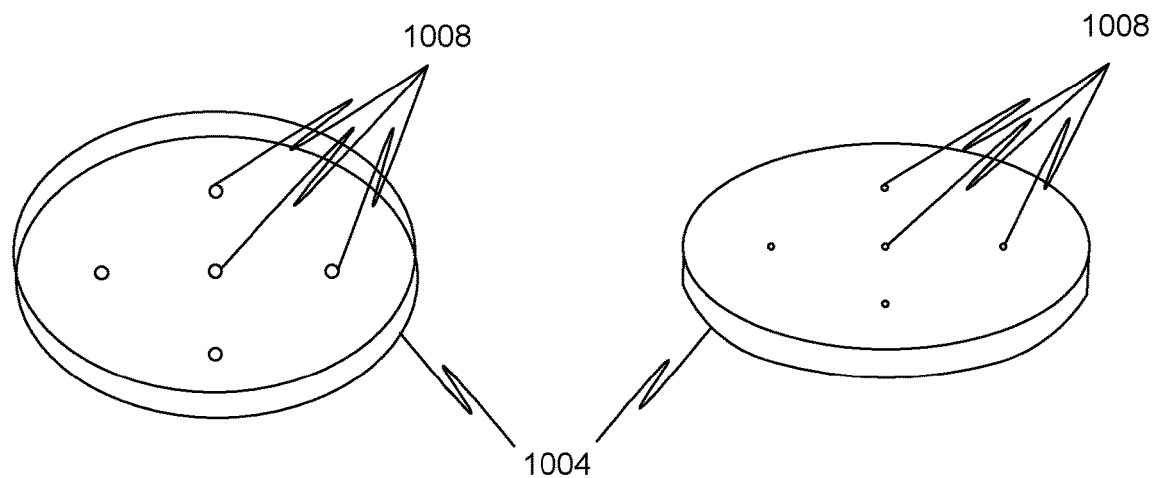
FIG. 10C  FIG. 10D

SYSTEM FOR TRANSCRANIAL STIMULATION

CROSS REFERENCE TO RELATED APPLICATIONS

This application claims priority to and the benefit of U.S. Provisional Patent Application Ser. No. 62/243,792, filed on 15 Dec. 2016.

FIELD

The aspects of the embodiments in the present disclosure pertain in general to the field of stimulation electrodes, and especially to a system for transcranial stimulation comprising a hydrophilic material.

BACKGROUND OF THE INVENTION

Transcranial direct current stimulation (tDCS) is a form of neurostimulation which includes, for example, delivering a constant and low current directly to a brain region of a person, namely a subject, through electrodes. The low current is normally in a range of 0.5 mA to 2 mA. tDCS is useful, for example, for treating patients with brain injuries (such as strokes), for treating depression, anxiety, tinnitus, chronic pain, and for enhancing language and mathematical abilities, for addressing attention span problem, for enhancing problem solving abilities, for improving memory, and for enhancing a coordination of body movements.

Known stimulation electrodes use conductive materials such as gels, spray or wet pads for creating better electrical contact between the electrode and a scalp of a patient. Typically, a large amount of the conductive gel or similar needs to be used in order to create a good electrical contact. This may cause discomfort some patients who have a lot of hair on their body and may force them to shower after the procedure to remove the conductive material from the hair and the scalp. Additionally, these materials are hard to apply correctly in order to ensure a good contact between the electrode and the scalp. They are normally applied in a trial and error approaches where an operator uses a small amount and then places the electrode on the conductive material and tests the conduction level. This process may be repeated by adding more of the conductive material until the desired conduction level is achieved. This is a tiresome approach and takes a long time, resulting in additional stress for the operator and the patient. A further problem when using pads is that the aqueous solution used to wet the pads easily spreads and forms a shunt via which the electrical current passes. This leads to a situation where a majority of the electrical current does not pass to the brain at all.

Therefore, in light of the foregoing discussion, there exists a need to overcome the aforementioned drawbacks.

SUMMARY

The present disclosure seeks to provide a system for facilitating administration of transcranial stimulation. Additionally, the present disclosure seeks to provide a kit that may be used to assemble the system for facilitating administration of transcranial stimulation. Moreover, the present disclosure seeks to provide a method for preparing the headcap for transcranial stimulation. The present disclosure provides a system that makes it easy and fast to prepare a headcap for transcranial stimulation.

Accordingly, in one aspect, an embodiment of the present disclosure is a system for facilitating administration of transcranial stimulation. The system comprises an electrode for transcranial stimulation and a distributor. The electrode comprises a counterpart configured to be attached to the headcap. Further, the electrode comprises a gel cup configured to be attached to the counterpart, the gel cup comprising an interior space. Further, the electrode comprises an electrical conductor configured to be disposed within the interior space of the gel cup. Further, the electrode comprises a gel pad comprising a hydrophilic material, the gel pad being arranged to be in contact with the electrical conductor. The distributor is configured to be removably attached to the gel cup, and comprises at least one inlet for an aqueous solution, and a plurality of outlets in a fluid communication with the at least one inlet, wherein the outlets are configured to direct the aqueous solution towards the gel pad.

In a further embodiment, an embodiment of the present disclosure is a kit comprising the system for facilitating administration of transcranial stimulation as disclosed above and a container for the aqueous solution. The container is removably connectable to the inlet of the distributor.

In another aspect, an embodiment of the present disclosure is a method for preparing a headcap for transcranial stimulation. The method comprises attaching a counterpart on the headcap, at each position for an electrode. The method further comprises attaching a gel cup, having a first side and a second side, to the counterpart by its second side. Further, the method comprises arranging a printed circuit board in the gel cup and arranging a gel pad made of a hydrophilic material having a first state and a second expanded state, on the printed circuit board. Moreover, the method comprises attaching distributor for distributing an aqueous solution for inducing expansion of the gel pad, to the gel cup, on the first side of the gel cup. The distributor comprises one or more inlets for the aqueous solution, and two or more outlets for the aqueous solution, wherein the outlets are arranged to direct the aqueous solution towards the gel pad. The method also comprises attaching a container for the aqueous solution on the inlet for the aqueous solution. The method further comprises injecting the aqueous solution into the distributor, maintaining the distributor in place for a pre-determined period of time, and removing the distributor.

Embodiments of the present disclosure substantially eliminate or at least partially address the aforementioned problems in the prior art. The disclosed system, kit, and method provide an easy and efficient way of preparing a headcap for transcranial stimulation. The gel pad is placed in the gel cup and soaked with the distributor, whereby the gel pad expands to its operational state. As the gel pad expands, it is retained in the gel cup, due to the cup-form of the gel cup, and the headcap is ready for use. The use of the distributor makes the process fast and reliable. Further, it ensures that no liquid escapes from the system.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein:

FIG. 10A is a top perspective view of a main body of a distributor according to an embodiment.

FIG. 10B is a bottom perspective view of the main body of FIG. 10A.

FIG. 10C is a top perspective view of an enclosure of the distributor of FIG. 10A.

FIG. 10D is a bottom perspective view of the enclosure of FIG. 10C.

Figure 1:
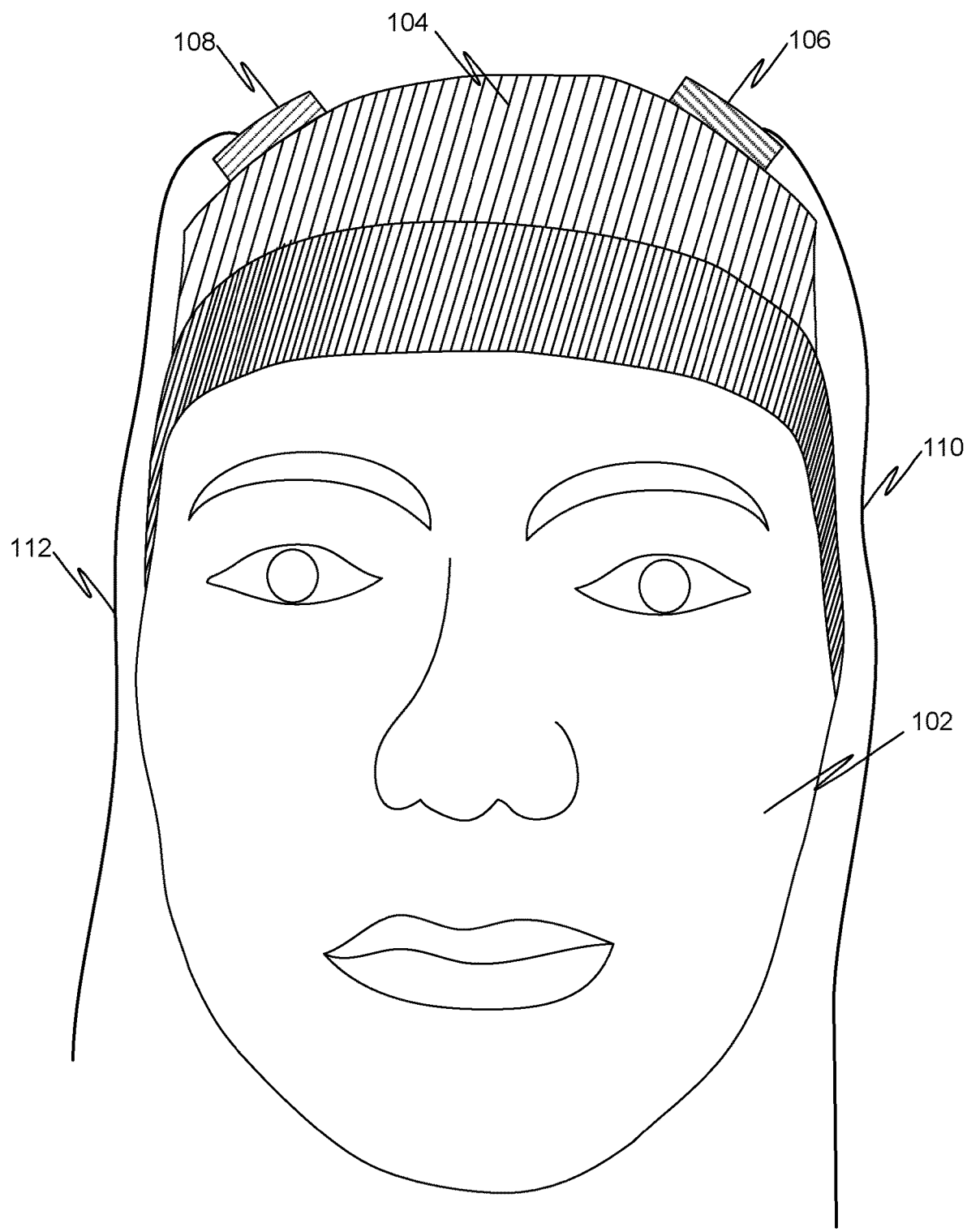
FIG. 1 is a front view of a patient's head wearing a headcap for transcranial stimulation according to an embodiment.

In the accompanying drawings, a non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein, as understood by the ordinary artisan based on the contextual use of such term, differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in, the context of transcranial stimulation, embodiments of the present disclosure are not limited to use only in this context.

In one aspect, an embodiment of the present disclosure is a system for facilitating administration of transcranial stimulation. The system comprises an electrode for transcranial stimulation and a distributor. The electrode comprises a counterpart configured to be attached to the headcap. Further, the electrode comprises a gel cup configured to be attached to the counterpart, the gel cup comprising an interior space. Further, the electrode comprises an electrical conductor configured to be disposed within the interior space of the gel cup. Further, the electrode comprises a gel pad comprising a hydrophilic material, the gel pad being arranged to be in contact with the electrical conductor. The distributor is configured to be removably attached to the gel cup, and comprises at least one inlet for an aqueous solution, and a plurality of outlets in a fluid communication with the at least one inlet, wherein the outlets are configured to direct the aqueous solution towards the gel pad.

The present system thus comprises a gel cup, which has a cup-like form, i.e. a bottom and sides. According to an embodiment, the gel cup has an essentially rounded shape, although it may have also another shape, such as elliptical, square, rectangular or triangular. It may also have an irregular shape. Most typically, the shape is however circular. Both the electrical conductor and the gel pad are arranged in the gel cup, prior to using the distributor for soaking the gel pad, i.e. to expand it to its second state, i.e. expanded state. For example, the diameter of the gel cup may be in the range 30-60 mm, and the height of its side may be in the range 8-9 mm.

The system may further comprise a headcap configured to be worn over a head portion of a user. Similarly, the counterpart can comprise attaching means configured to attach the counterpart to the headcap. The attaching means may include, but is not limited to, sewing, using Velcro fastener, using safety pins, and pasting using glue.

The electrode may also comprise a printed circuit board (PCB) disposed within the interior space of the gel cup, wherein a surface of the PCB comprises the electrical conductor; and an electrical cable comprising a first end and a second end, wherein the first end is electrically connected to the electrical conductor, wherein the second end of the cable is configured to be connectable to an output terminal of a transcranial direct current stimulator.

According to an embodiment, the electrode further comprises a frame part, wherein the gel cup comprises a first side and a second side, wherein the second side is attached to the counterpart, wherein the first side is attached to the frame part. The function of the frame part is to further secure the gel pad in the gel cup. The frame part may also be integral of the gel cup. Accordingly, the gel cup may have, around the edges of its sides (or side if the gel cup is circular), a large extension towards the centre of the gel cup. The frame part may also be a separate part that may be attached to the gel cup by, for example, a snap joint or by threads.

In one embodiment, the distributor comprises a main body and an enclosure attached to the main body to form the fluid communication, wherein the main body comprises the at least one inlet, wherein the enclosure comprises the plurality of outlets. The plurality of outlets can be evenly arranged over a surface of the distributor, wherein the surface faces the interior space while the distributor is attached to the gel cup. The number of the plurality of outlets can be for example in the range of three to ten.

According to an embodiment, the distributor thus comprises one or more inlets for the aqueous solution, although it is believed that one inlet would be optimal. The distributor may also comprise two or more outlets for the aqueous solution, such as three to ten outlets. For example, there may be three, four, five, six, seven, eight, nine or ten outlets, or even more if needed. Preferably, the outlets are distributed evenly on the distributor, i.e. on the inner surface of the distributor. The inner surface is the side that is on the side of the gel pad and possibly also in contact with the gel pad.

In one embodiment, In one embodiment, a first diameter of each outlet is smaller than a second diameter of the inlet, in other words, the diameter of each outlet for the aqueous solution is smaller than the diameter of the inlet for the aqueous solution. The diameters of the inlet and of the outlets are preferably selected such that the distributor allows even distribution of the aqueous solution on the gel pad. The distributor thus takes into account the pressure with which the aqueous solution is injected into the distributor, and evenly distributes it. According to one embodiment, the diameter of each outlet is identical or essentially identical. According to another embodiment, the diameter of the outlets differs depending on the location of the outlet. For example, there may be one smaller outlet (with a diameter of for example 0.5 mm) in the middle and a few slightly larger outlets (with a diameter of for example 0.7 mm) closer to the periphery.

According to yet another embodiment, the hydrophilic material comprises a superporous hydrogel. Such materials are known in the art and some are described for example in WO 2015/173335. The hydrogels constitute a broad class of materials, which may be completely water soluble or swell extensively in water but are not completely water soluble. They have been used in a variety of medical applications. Medical electrodes are used to transmit electrical currents between the body of a patient and an external medical equipment and hydrogels are often used as conductive compositions with medical electrodes. Typically, the hydrophilic material has a first state and a second expanded state, the expansion being induced by an aqueous solution.

An embodiment of the present disclosure is a kit comprising the system for facilitating administration of transcranial stimulation as disclosed above and a container for the aqueous solution. The container is removably connectable to the inlet of the distributor.

According to a further embodiment, the container is in the form of a bottle or a syringe. In case a bottle is used, it preferably contains the required amount of aqueous solution for soaking the gel pad, and is made of a material that allows it to be squeezed, when the gel pads are to be expanded. The kit may also comprise a pipe arrangeable between the container and the inlet of the distributor. Such a pipe typically has a relatively small length, such as 5-10 cm, and it is mainly used for increasing the ease of use. In a further embodiment, the kit comprises also a headcap. The headcap may comprise 2-8 electrodes. The electrodes are attachable to the headcap in any suitable manner, such as by sewing. According to one embodiment, the contained is configured to hold an aqueous solution, wherein the container comprises a mouth configured to couple with the at least one inlet to facilitate flow of the aqueous solution into the at least one inlet.

In another aspect, a method for preparing a headcap for transcranial stimulation is disclosed. The method comprises attaching a counterpart on the headcap, at each position for an electrode. The method further comprises attaching a gel cup, having a first side and a second side, to the counterpart by its second side. Further, the method comprises arranging a printed circuit board in the gel cup and arranging a gel pad made of a hydrophilic material having a first state and a second expanded state, on the printed circuit board. Moreover, the method comprises attaching distributor for distributing an aqueous solution for inducing expansion of the gel pad. The distributor may be attached to the gel cup, on the first side of the gel cup. The distributor comprises one or more inlets for the aqueous solution, and two or more outlets for the aqueous solution, wherein the outlets are arranged to direct the aqueous solution towards the gel pad. The method also comprises attaching a container for the aqueous solution on the inlet for the aqueous solution. The method further comprises injecting the aqueous solution to the distributor, maintaining the distributor in place for a pre-determined period of time, and removing the distributor.

According to a further embodiment, the pre-determined period of time is from 10-60 seconds. For example, the pre-determined period of time may be from 10, 15, 20, 25, 30, 35, 40, 45 or 50 seconds up to 15, 20, 25, 30, 35, 40, 45, 50, 55, or 60 seconds. In some embodiments, depending on the type of gel pad used, the time may be shorter or longer. The aim of this pre-determined period, during which the distributor is maintained in place after injection of the aqueous solution, is to ensure that the gel pad swells to its expanded state in an even manner. The distributor thus functions as a cover for the gel cup, preventing the gel pad to expand more in one direction than another.

In other words, the disclosure relates to a system for a headcap for transcranial stimulation. The system comprises an electrode for transcranial stimulation and a distributor. The electrode comprises a counterpart attachable on the headcap. Further, the electrode comprises a gel cup having a first side and a second side, and attachable to the counterpart by its second side. Further, the electrode comprises a printed circuit board, arrangeable in the gel cup. Further, the electrode comprises a gel pad made of a hydrophilic material having a first state and a second expanded state, arrangeable on the printed circuit board. The distributor is for distributing an aqueous solution for inducing expansion of the gel pad. The distributor may be removably attachable to the gel cup on its first side. The distributor comprises one or more inlets for the aqueous solution, and two or more outlets for the aqueous solution, wherein the two or more outlets are arranged to direct the aqueous solution towards the gel pad.

DETAILED DESCRIPTION OF EMBODIMENTS

Referring now to the drawings, FIG. 1 is a front view of a patient's head 102 wearing a headcap 104 for transcranial stimulation, according to an embodiment. The headcap 104 includes an electrode 106. The headcap 104 may include two or more electrodes; for example, electrodes 106-108. A cable 110 may connect the electrode 106 with a main tDCS transcranial direct current stimulator. Similarly, a cable 112 may connect the electrode 108 with the main tDCS transcranial direct current stimulator.

Figure 2A:
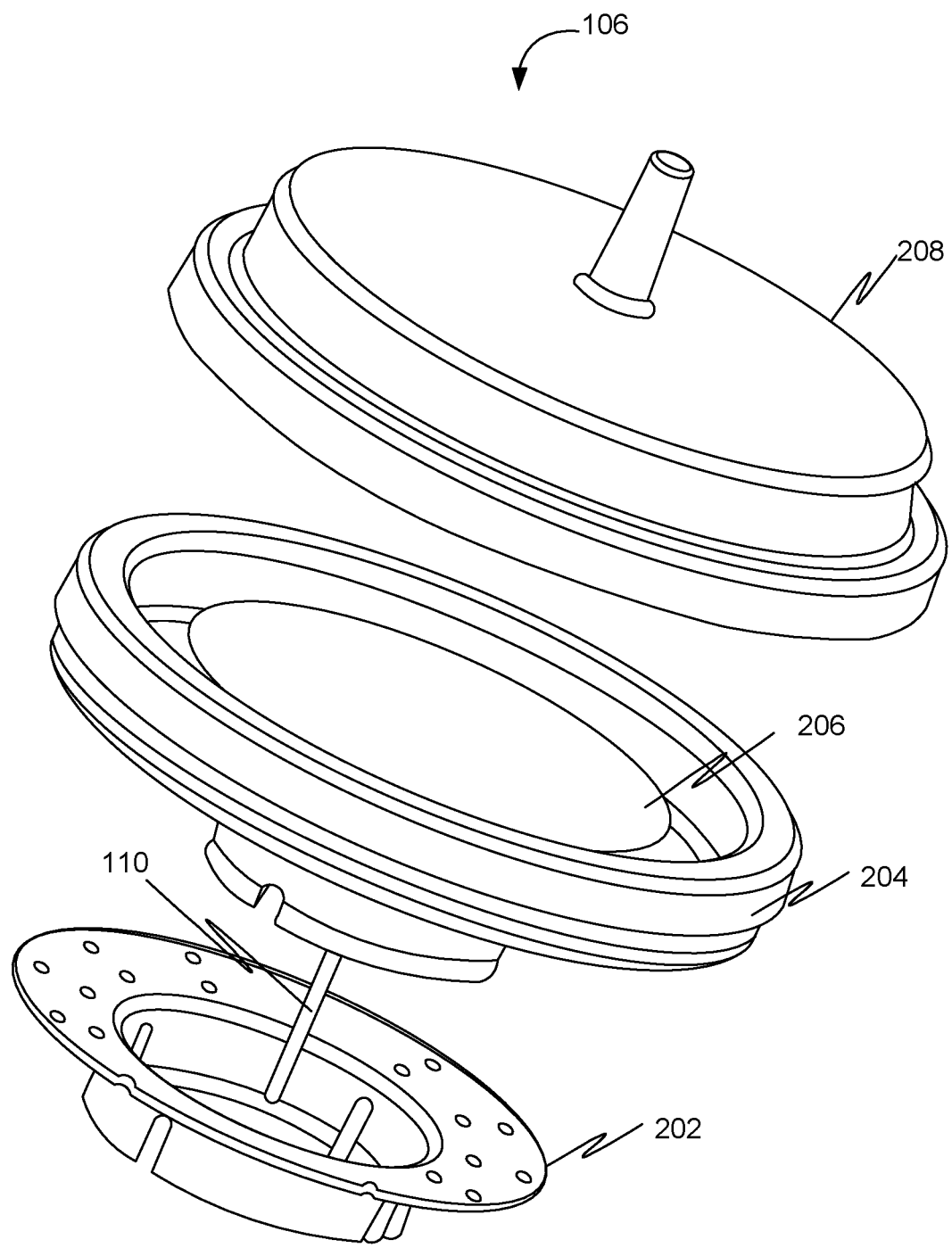
FIG. 2A is an exploded, top perspective view of an electrode for transcranial stimulation according to an embodiment.
Figure 2B:
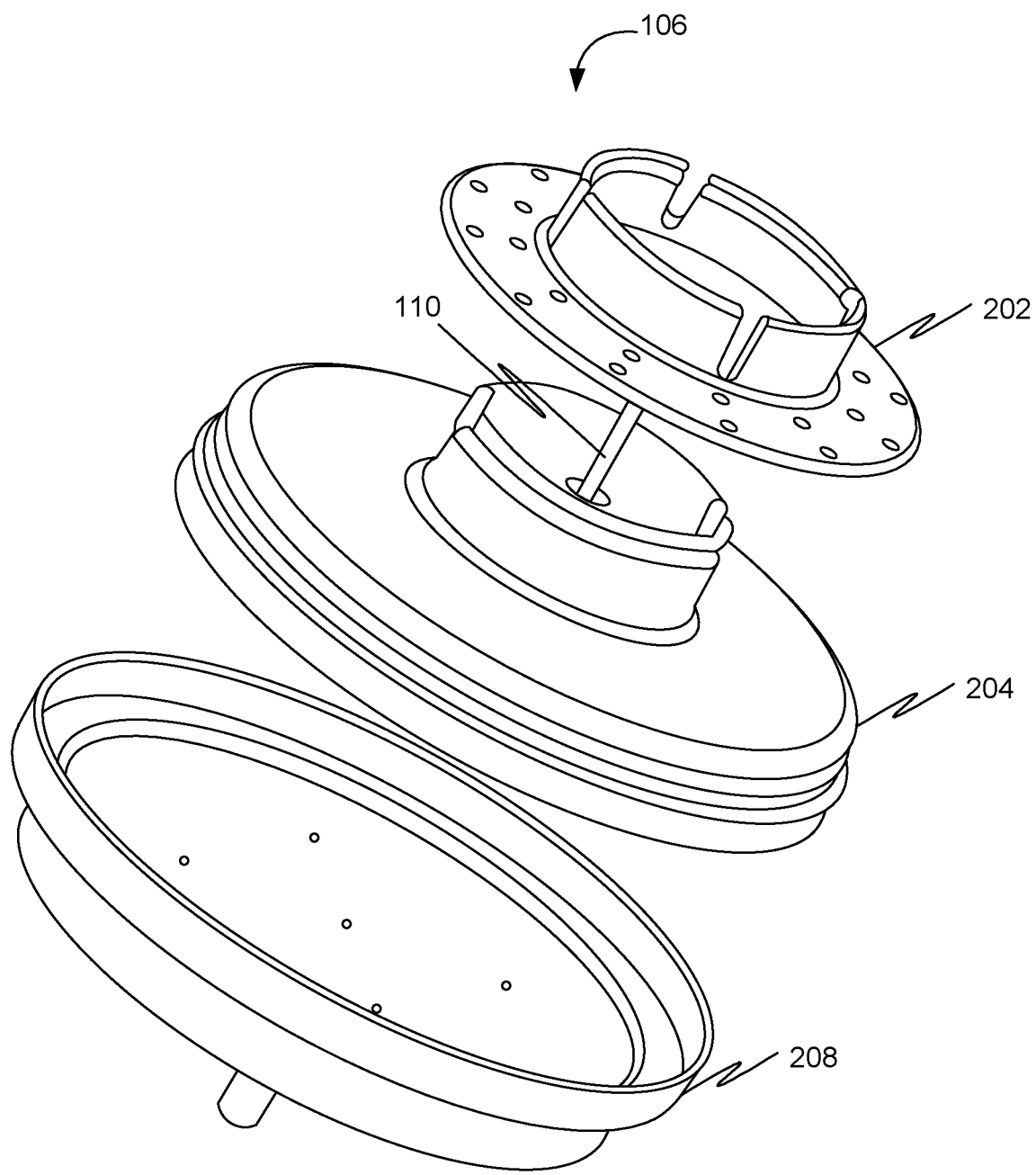
FIG. 2B is an exploded, bottom perspective view of the electrode of FIG. 2A.
Figure 3:
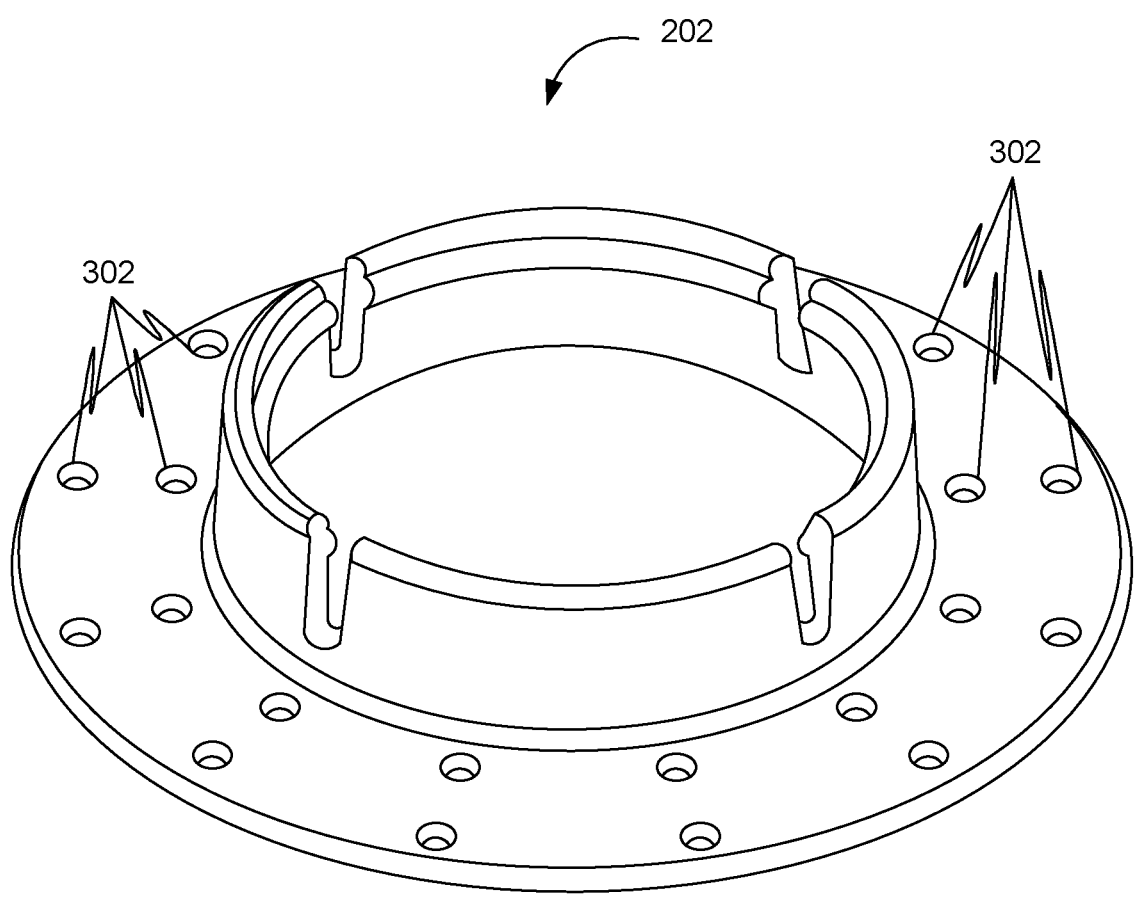
FIG. 3 is a perspective view of a counterpart of the electrode of FIGS. 2A-B.
Figure 4:
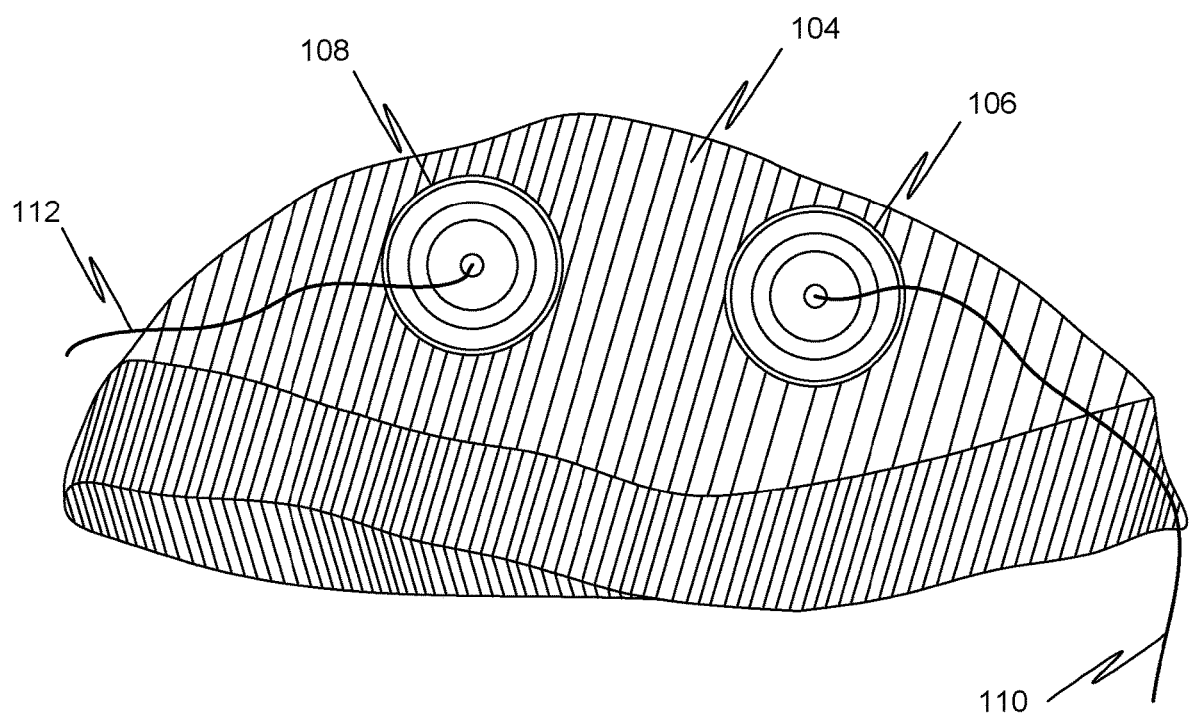
FIG. 4 is a top view of the headcap of FIG. 1 in a folded state, when not in use.

FIG. 2A is an exploded, top perspective view of an electrode 106 for transcranial stimulation according to an embodiment. FIG. 2B is an exploded, bottom perspective view of the electrode 106. The electrode 106 includes a counterpart 202 attachable on the headcap 104. The counterpart 202 may be sewn to the headcap 104 at a specific location. Further, multiple counterparts 202 may be sewn to the headcap 104. The counterpart 202 may have holes 302 (shown in FIG. 3) through which a thread may be sewn to attach the counterpart 202 to the headcap 104. FIG. 3 is a perspective view of the counterpart 202. Further, two counterparts 202 may be sewn to the headcap 104 at the left and right prefrontal cortex positions for depression treatment, as shown in FIG. 4. FIG. 4 is a top view of the headcap 104 in a folded state, when not in use.

Figure 5A:
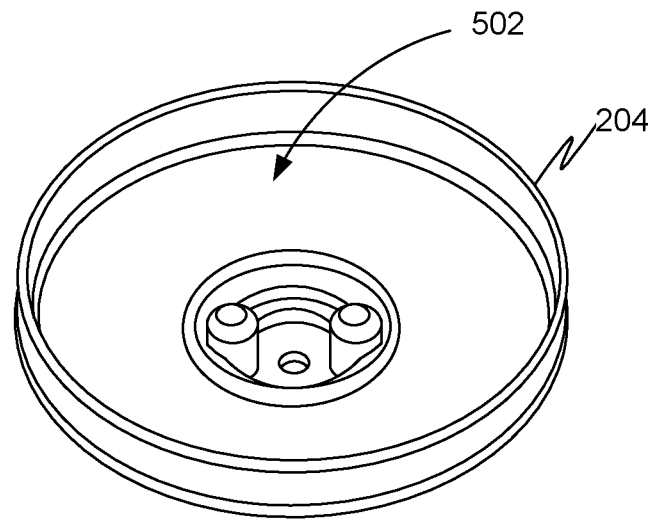
FIG. 5A is a top perspective view of a gel cup of the electrode of FIGS. 2A-B.
Figure 5B:
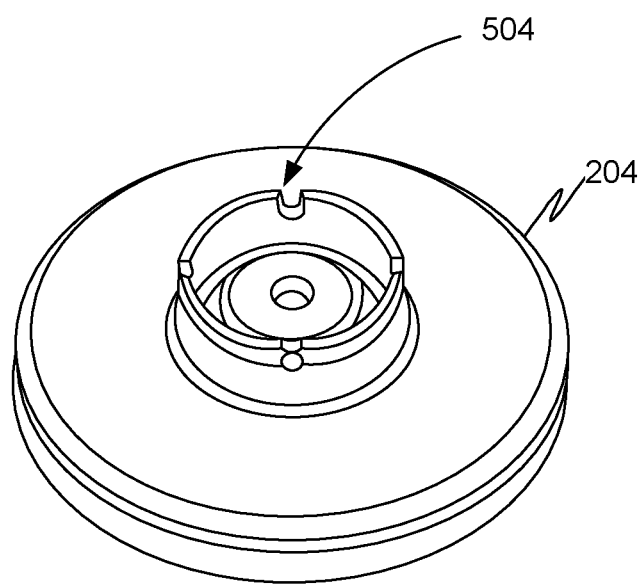
FIG. 5B is a bottom perspective view of the gel cup of the electrode of FIGS. 2A-B.
Figure 6:
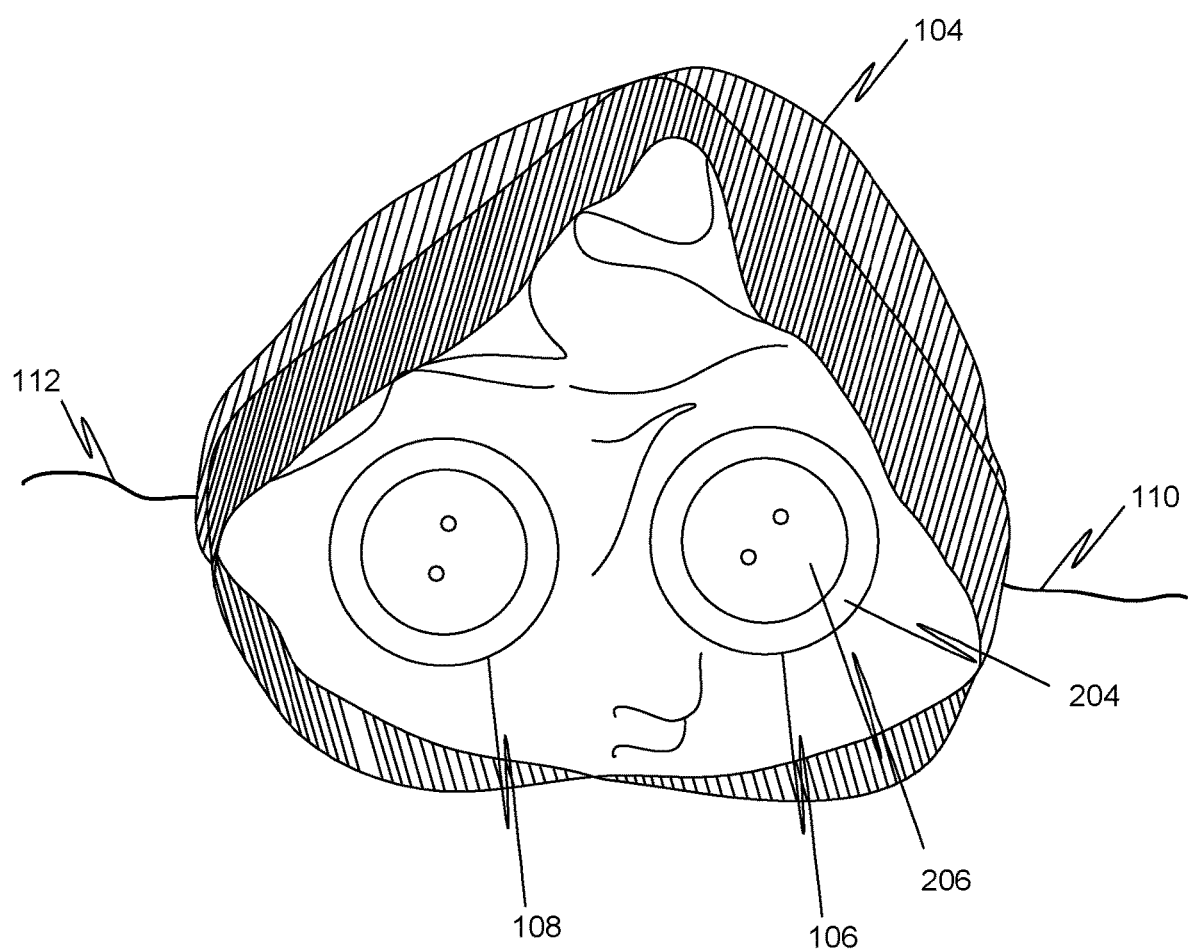
FIG. 6 is a top view of the inside of the headcap of FIG. 1.

Further, the electrode 106 includes a gel cup 204. FIGS. 5A-B are perspective views of the gel cup 204. The gel cup 204 has a first side 502 (shown in FIG. 5A) and a second side 504 (shown in FIG. 5B). The gel cup 204 is attachable to the counterpart 202 by the second side 504. For example, the height of the side of the gel cup 204 may be 8-9 mm, and the diameter may be 30-60 mm. As shown in FIG. 6, the gel cup 204 may be attached to the counterpart 202 from the inside of the headcap 104, so the position of the gel cup 204 on the patient's head may be consistent and determined by the headcap (104)—counterpart (202) configuration. FIG. 6 is a top view of the inside of the headcap 104.

Figure 7A:
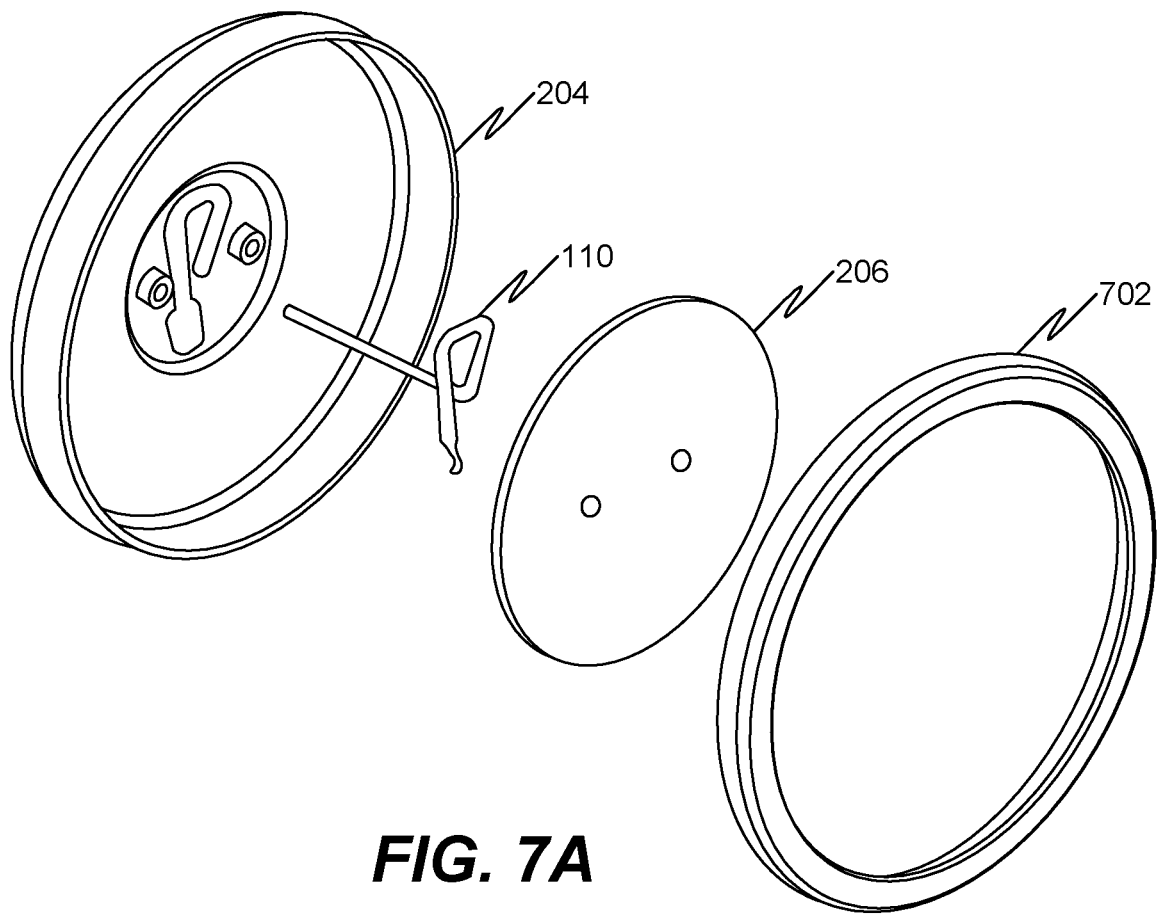
FIG. 7A is an exploded, schematic illustration of a gel cup, a printed circuit board and a frame part, of the electrode of FIGS. 2A-B.
Figure 7B:
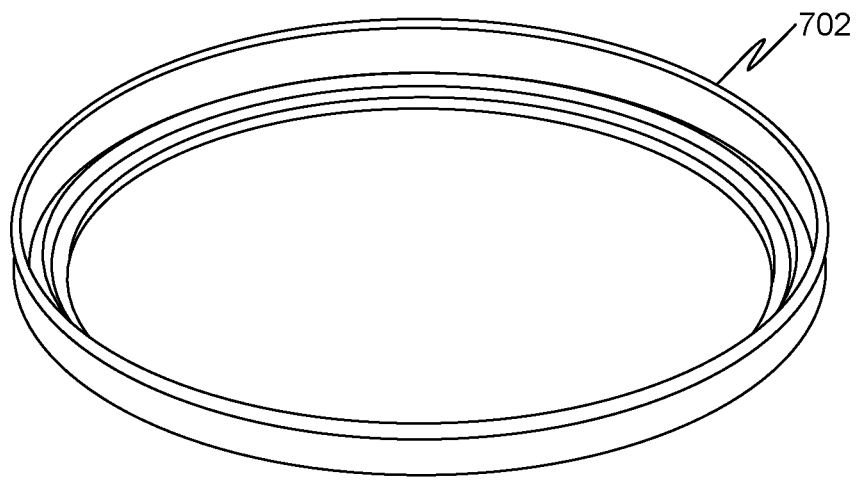
FIG. 7B is a perspective view of the frame part of FIG. 7A.
Figure 8:
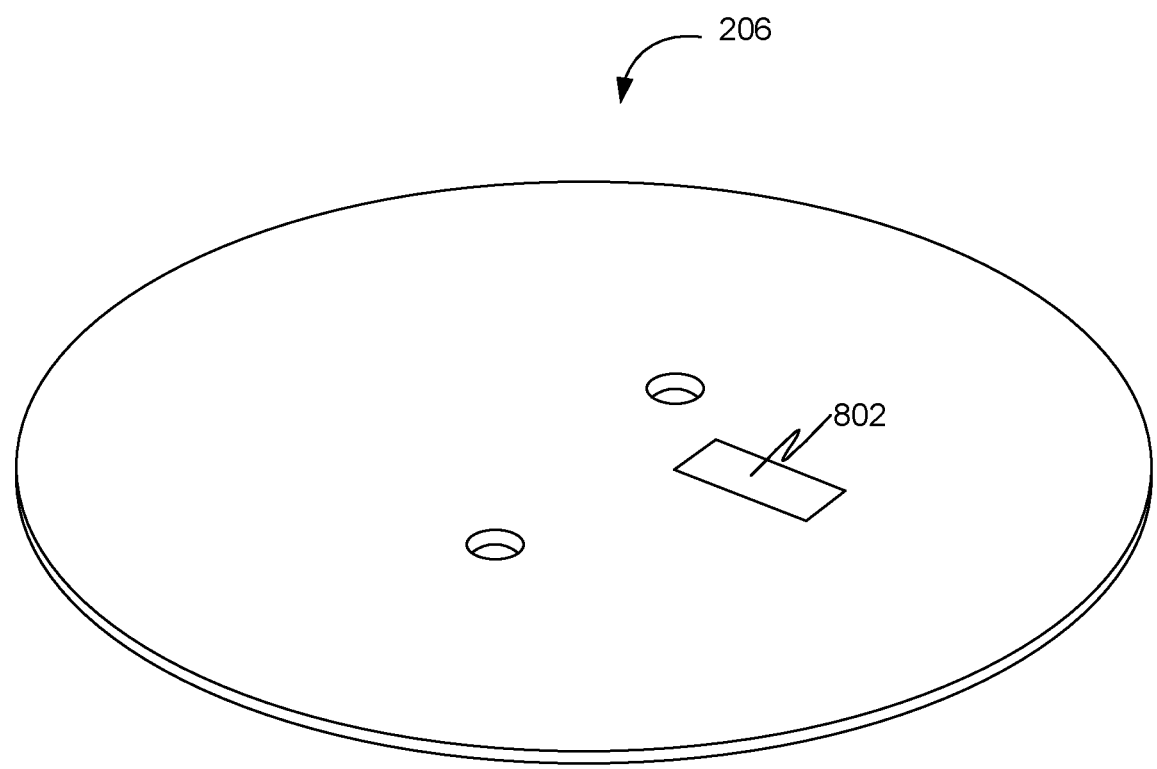
FIG. 8 is a perspective view of the printed circuit board of the electrode of FIGS. 2A-B.

Moreover, the electrode 106 includes a printed circuit board (PCB) 206, arrangeable in the gel cup 204. The PCB 206 may be assembled to the bottom of the gel cup 204. Further, the electrode 106 may include a frame part 702 attachable on the first side 502 of the gel cup 204, as shown in FIGS. 7A and 7B. FIG. 7A is an exploded, schematic illustration of the gel cup 204, the PCB 206 and the frame part 702, of the electrode 106. FIG. 7B is a perspective view of the frame part 702. The frame part 702 may be attached to the edge of the gel cup 204 to ensure that when the gel cup 204 is placed against the patient's head 102, the contacting surface is not a sharp edge, but a slightly wider and more comfortable contact surface. The frame part 702 may also assist in maintaining a gel pad in place. The cable 110 connected to the PCB 206 is connected to a main tDCS transcranial direct current stimulator. The PCB 206 includes one or more conductive surfaces 802, as shown in FIG. 8. FIG. 8 is a perspective view of the PCB 206 of the electrode 106.

Figure 9A:
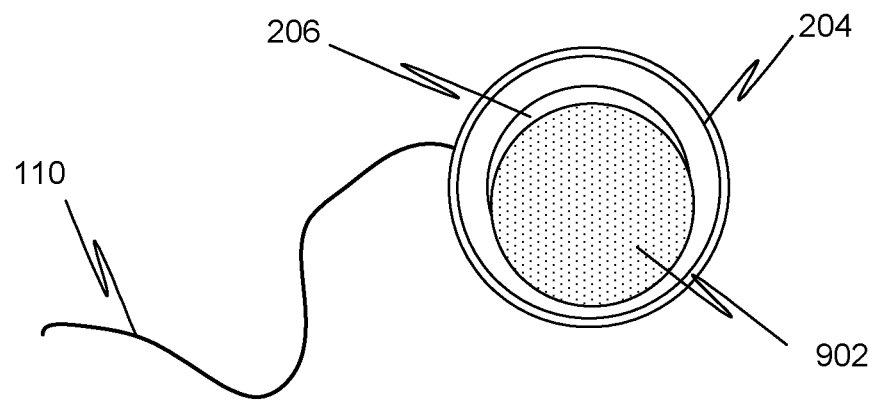
FIG. 9A is a top view of a gel pad placed on the printed circuit board of FIG. 8.
Figure 9B:
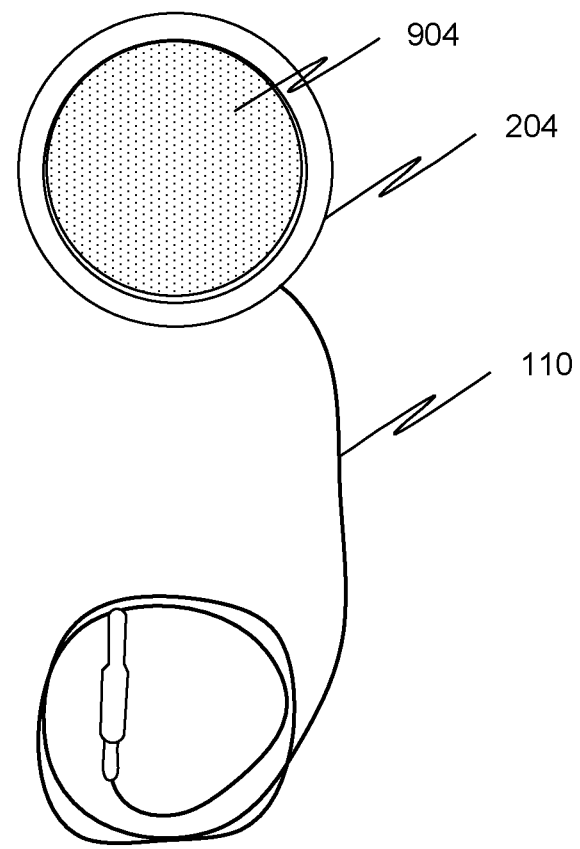
FIG. 9B is a top view of the gel pad of FIG. 9A in an expanded state.
Figure 17A:
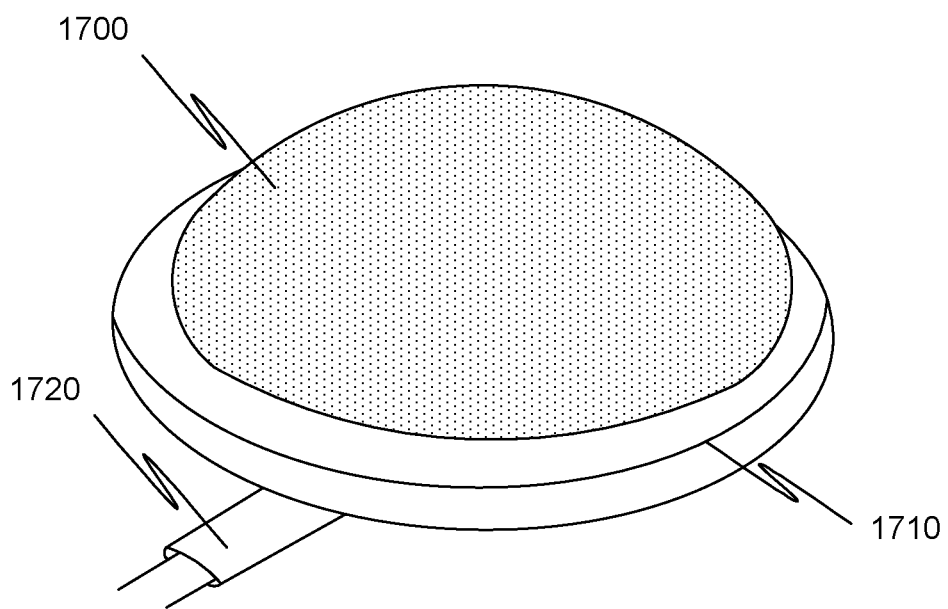
FIG. 17A is a top perspective view of a gel pad in an expanded state according to an embodiment.
Figure 17B:
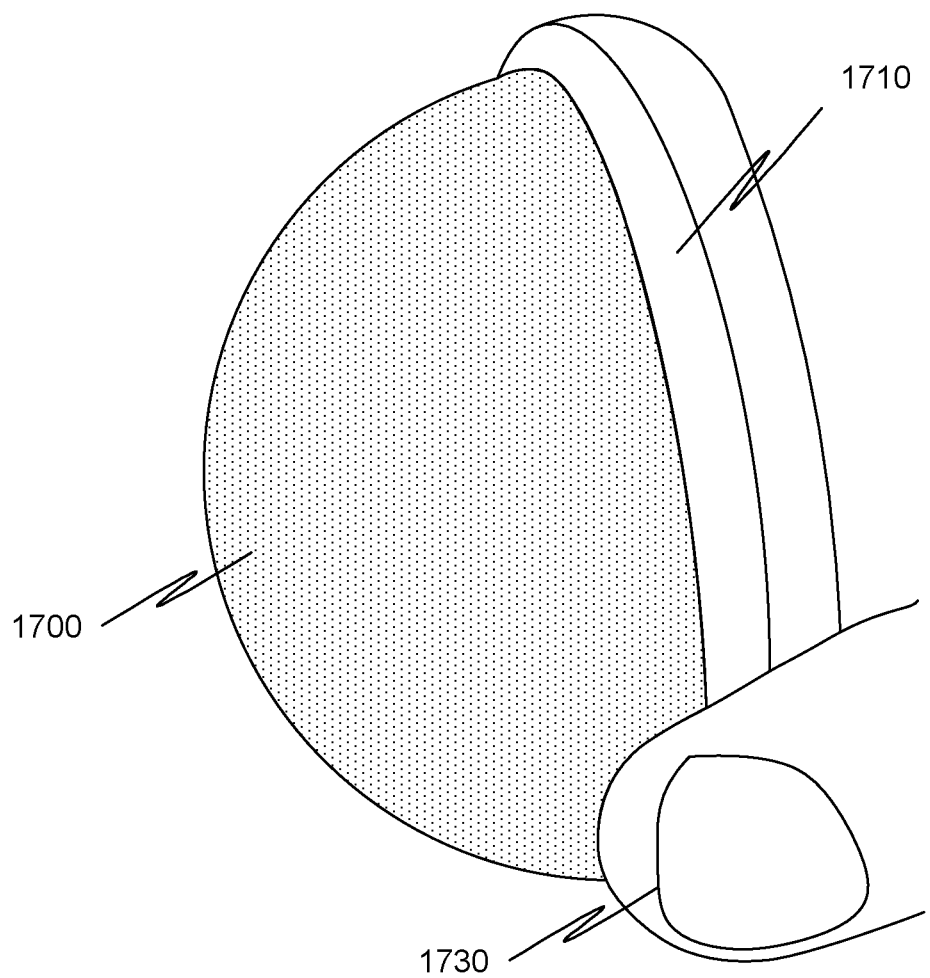
FIG. 17B is a side perspective view of the gel pad of FIG. 17A.

Yet further, the electrode 106 includes a gel pad 902 arrangeable on the PCB 206, as shown in FIG. 9A. The gel pad 902 is made of a hydrophilic material having a first state (shown in FIG. 9A) and a second expanded state 904 (shown in FIG. 9B). FIGS. 9A-B are top views of the gel pad 902 placed on the PCB 206. FIG. 17A is a top perspective view of a gel pad 1700 in an expanded state according to an embodiment. FIG. 17B is a side perspective view of the gel pad 1700. The gel pad 1700 is in arranged in top of housing 1710 which comprises PCB (not shown). Electrical connection is provided via wire 1720. In FIG. 17B a person is holding the housing 1710 with fingers 1730 to demonstrate typical size of the arrangement.

The gel pad 902 may be a disc-shaped pad made of superporous hydrogel. It is provided in its dry state (as shown in FIG. 9A), but after soaking with an aqueous solution it expands and softens (as shown in FIG. 9B). If the aqueous solution contains ions (e.g. saline solution), then electrical current may be conducted through the hydrogel. It is placed on top of the PCB 206 in the gel cup 204. The gel pad 902 with the PCB 206 forms the electrode 106.

FIGS. 2A-B also depict a distributor 208 for distributing an aqueous solution for inducing expansion of the gel pad 902. The distributor 208 may not be a part of the electrode 106. The distributor 208 being removably attachable to the gel cup 204 on its first side 502. The distributor 208 includes one or more inlets for the aqueous solution, and two or more outlets for the aqueous solution. For example, the distributor 208 may include three to ten outlets for the aqueous solution. The outlets are arranged to direct the aqueous solution towards the gel pad 902. Therefore, the outlets for the aqueous solution may be arranged evenly on the distributor 208. In general, the diameter of each outlet for the aqueous solution may be smaller than the diameter of the inlet for the aqueous solution.

Figure 18A:
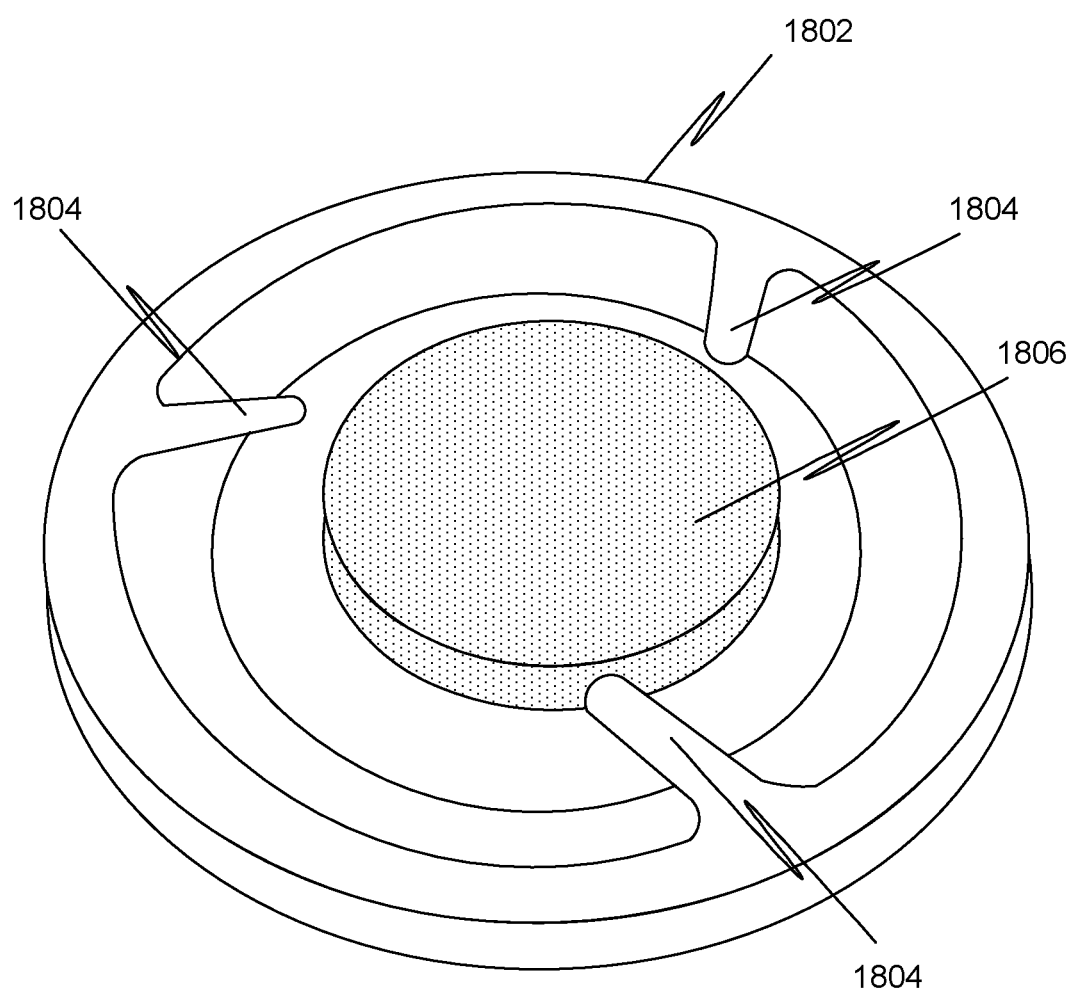
FIG. 18A is a top perspective view of a gel pad in a gel cup according to an embodiment.
Figure 18B:
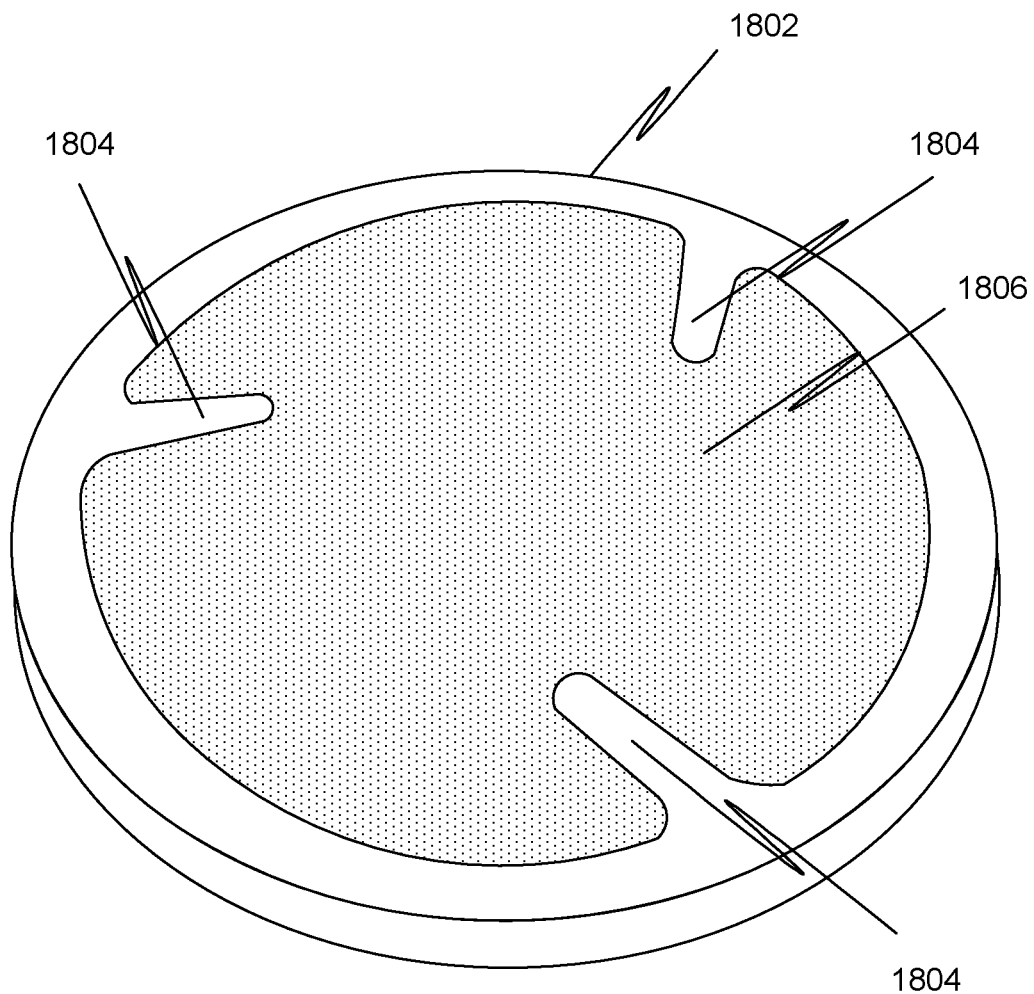
FIG. 18B is a top perspective view of the gel pad of FIG. 18A in an expanded state.

The distributor 208 may be a single part. Alternatively, the distributor 208 may include two parts, a main body 1002 and an enclosure 1004, as shown in FIGS. 10A-D. FIGS. 10A-B are perspective views of top and bottom sides of the main body 1002, respectively. FIGS. 10C-D are perspective views of top and bottom sides of the enclosure 1004, respectively. The main body 1002 may be designed to be a good fit with the gel cup 204. The main body 1002 may also include a cone-shaped inlet 1006 that may be attached to a plastic syringe or a container, such as a bottle. The enclosure 1004 may include outlets 1008, such that when an aqueous solution is injected into the distributor 208 from a plastic syringe through the cone-shaped inlet 1006, the aqueous solution then exits the distributor 208 with higher pressure through the small outlets 1008. For example, there may be 5 small outlets in the small outlets 1008. Further, a gel cup 1802 may include one or more protrusions 1804 to retain a gel pad 1806 in an expanded state as shown in FIGS. 18A-B.

Figure 11:
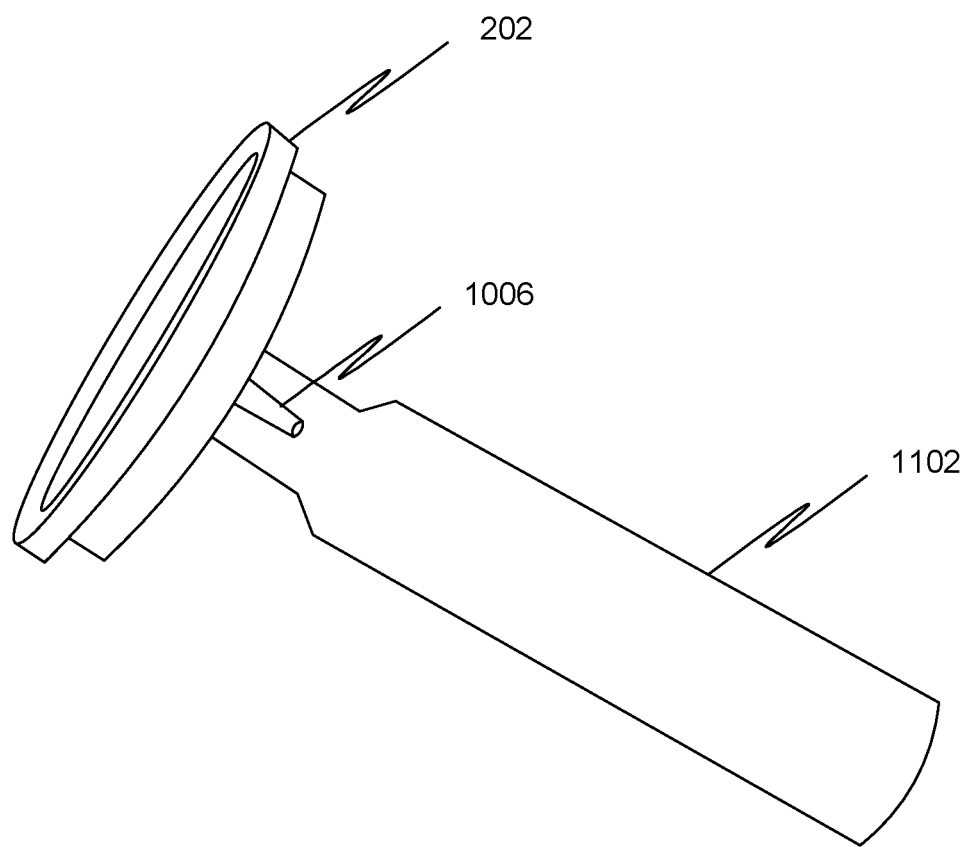
FIG. 11 is a perspective view of the distributor connected to a container, according to an embodiment.

In a further embodiment of the disclosure, a kit comprising one or more electrodes 106 and a container for the aqueous solution is disclosed. The container may be removably connectable to the inlet 1006 of the distributor 208 of the one or more electrodes 106. The container may include a pipe arrangeable between the container and the inlet 1006 of the distributor 208. For example, the container may be in the form of a bottle 1102, as shown in FIG. 11. FIG. 11 is a perspective view of the distributor 208 connected to the bottle 1102. The kit may further include the headcap 104. The headcap 104 may include one or more electrodes 106. For example, the headcap 104 may include 2-8 electrodes.

Figure 12:
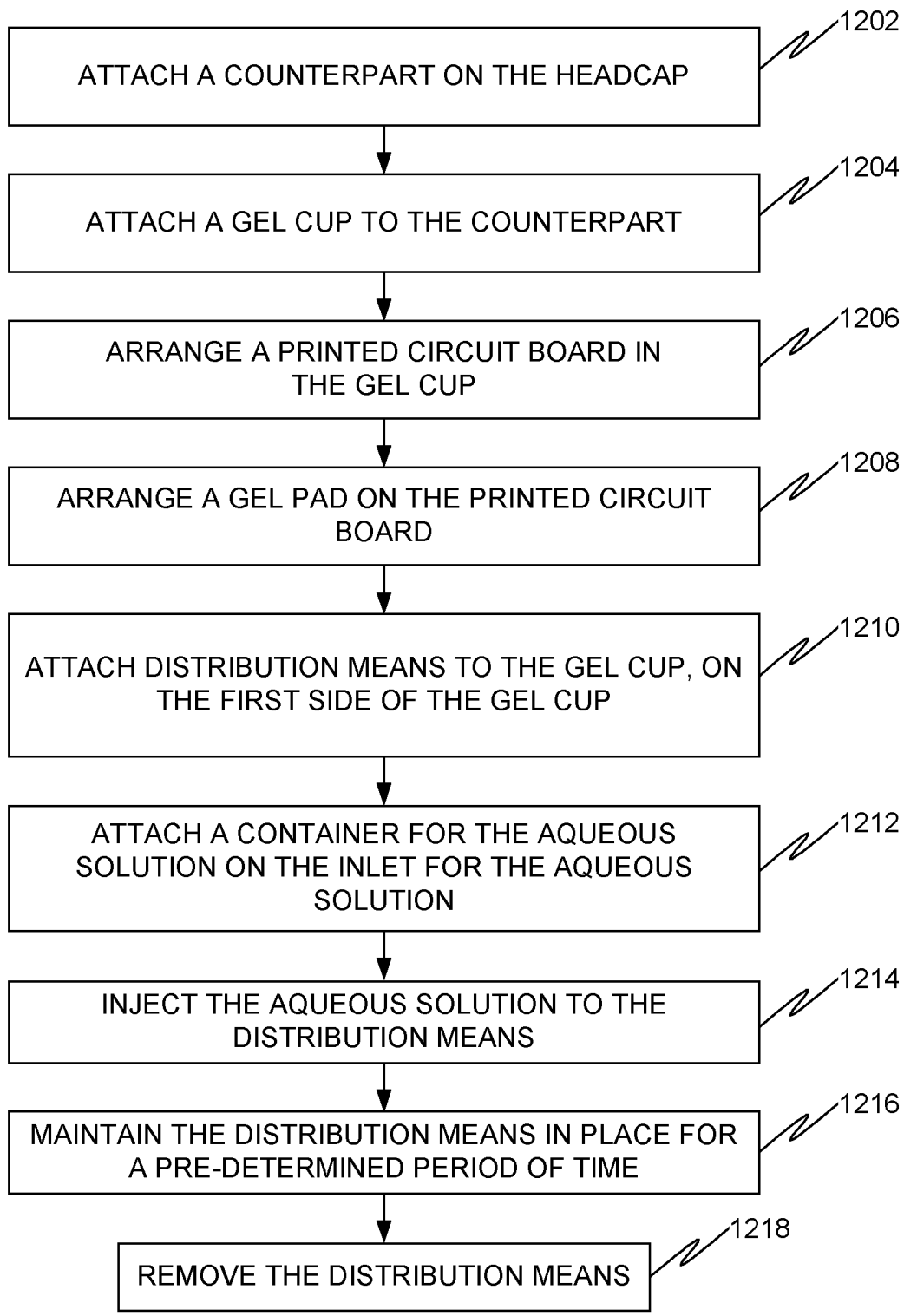
FIG. 12 is a flowchart for a method for preparing a headcap for transcranial stimulation, according to an embodiment.
Figure 13A:
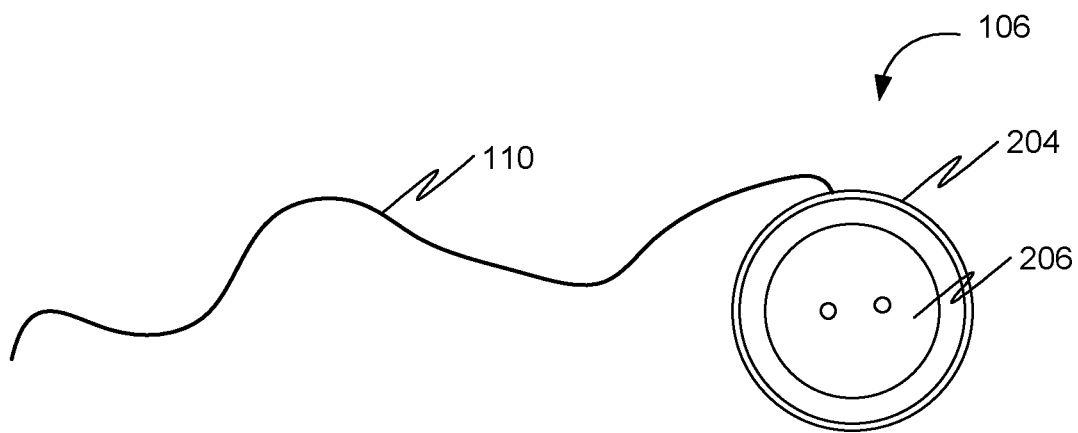
FIG. 13A is a top view of an electrode showing a printed circuit board placed in a gel cup of for transcranial stimulation, according to an embodiment.
Figure 13B:
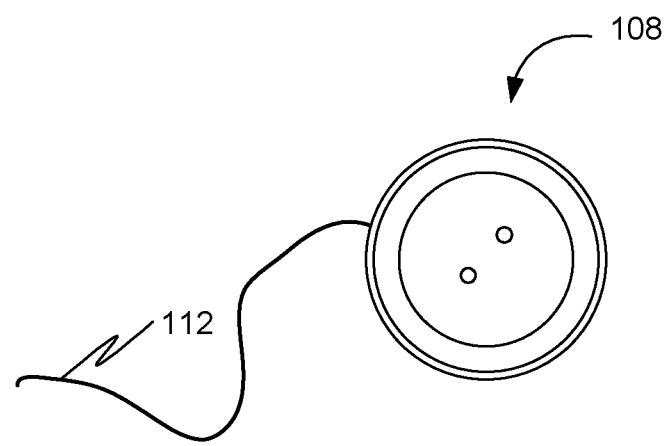
FIG. 13B is a top view of an electrode showing a printed circuit board placed in a gel cup for transcranial stimulation, according to an embodiment.

FIG. 12 is a flowchart for a method 1200 for preparing a headcap 104 for transcranial stimulation. At 1202, the method 1200 includes attaching the counterpart 202 on the headcap 104, at each position for the electrode 106, as shown in FIG. 4. At 1204, the method 1200 includes attaching the gel cup 204, having the first side 502 and the second side 504, to the counterpart 202 by its second side 504, as shown in FIG. 6. At 1206, the method 1200 includes arranging the PCB 206 in the gel cup 204, as shown in FIG. 6. Once the headcap 104 has been prepared, i.e. the counterpart 202 is attached to it and the PCB 206 is arranged (typically attached by welding or similarly), these steps do not need to be repeated each time the headcap 104 is used. FIG. 13A is a top view of the electrode 106 showing the gel cup 204 with the PCB 206 attached to tDCS transcranial direct current stimulator via the cable 110. FIG. 13B is a top view of the electrode 108 showing a printed circuit board placed in the gel cup 204 for transcranial stimulation.

Figure 14:
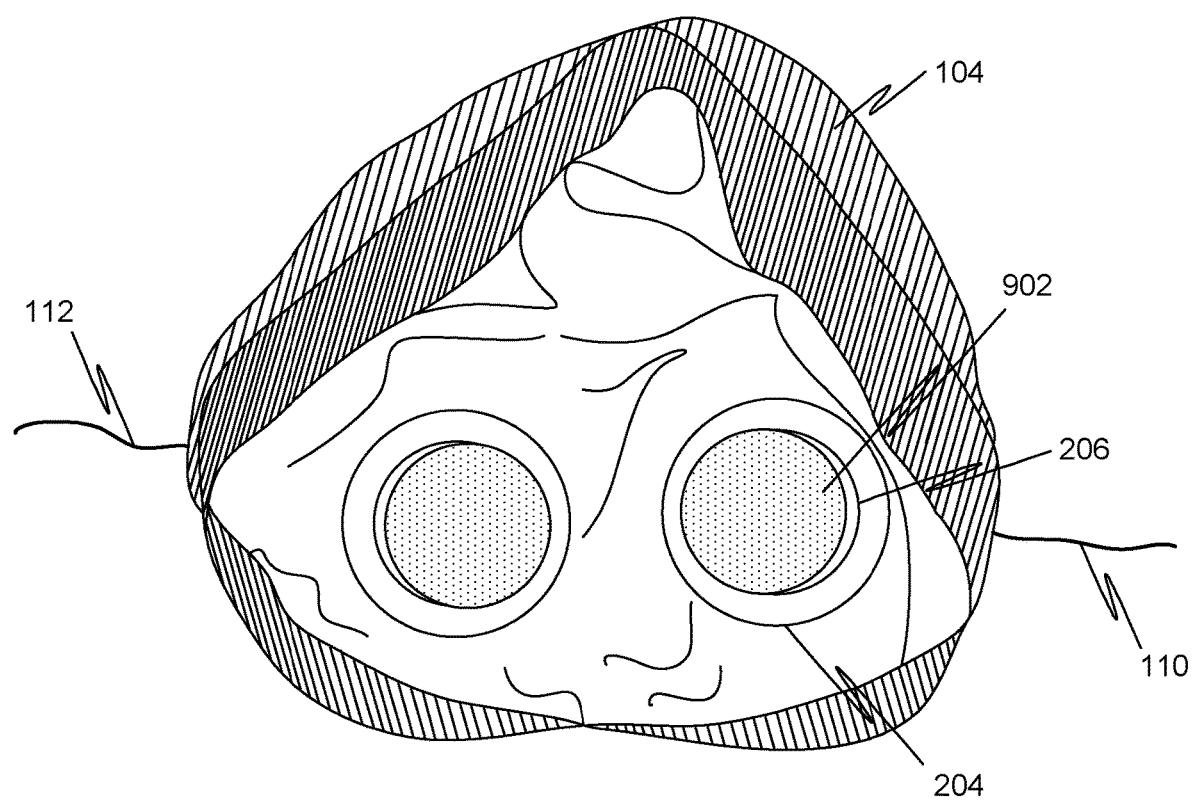
FIG. 14 is a top view of the inside of the headcap for transcranial stimulation, according to an embodiment.

At 1208, the method 1200 includes arranging the gel pad 902 made of a hydrophilic material having a first state and a second expanded state, on the PCB 206, as shown in FIG. 14. For example, one gel pad (hydrogel pad) in its dry state may be placed in each gel cup (including the gel cup 204). FIG. 14 is a top view of the inside of the headcap 104 for transcranial stimulation.

Figure 15:
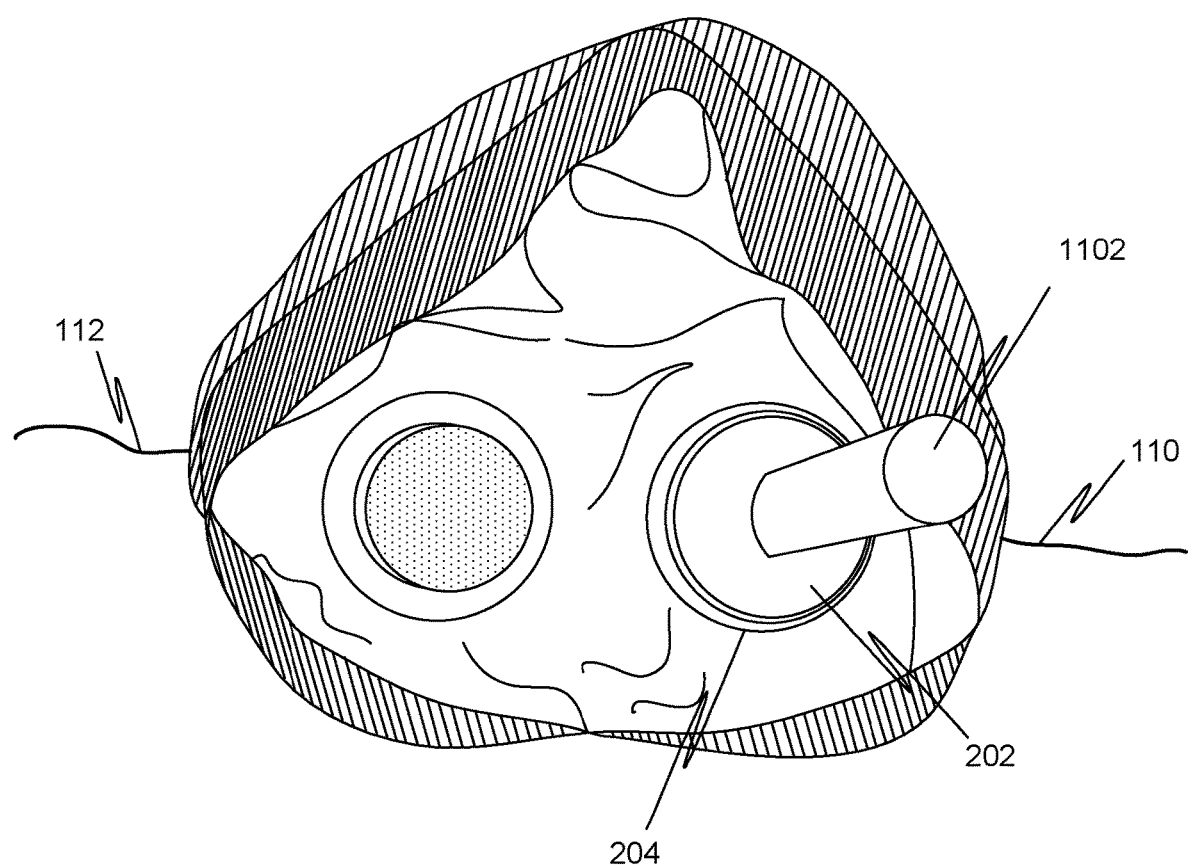
FIG. 15 is a top view of the inside of the headcap for transcranial stimulation, according to an embodiment.

At 1210, the method 1200 includes attaching the distributor 208 for distributing an aqueous solution for inducing expansion of the gel pad 902, to the gel cup 204, on the first side 502 of the gel cup 204, as shown in FIG. 15. The distributor 208 includes one or more inlets 1006 for the aqueous solution, and two or more outlets 1008 for the aqueous solution. The outlets 1008 are arranged to direct the aqueous solution towards the gel pad 902. At 1212, the method 1200 includes attaching a container (such as the bottle 1102) for the aqueous solution on the inlet 1006 for the aqueous solution, as shown in FIG. 11.

At 1214, the method 1200 includes injecting the aqueous solution to the distributor 208, as shown in FIG. 15. For example, the container may be pressed to soak the hydrogel with multiple moderate-pressure jets of saline solution. FIG. 15 is a top view of the inside of the headcap 104 for transcranial stimulation.

At 1216, the method 1200 includes maintaining the distributor 208 in place for a pre-determined period of time. This allows the hydrogel to swell in a restricted space. For example, the pre-determined period of time may vary from 10-60 seconds. After the hydrogel has been soaked and allowed to swell under the distributor 208, it expands in volume, and becomes soft and porous.

Figure 16:
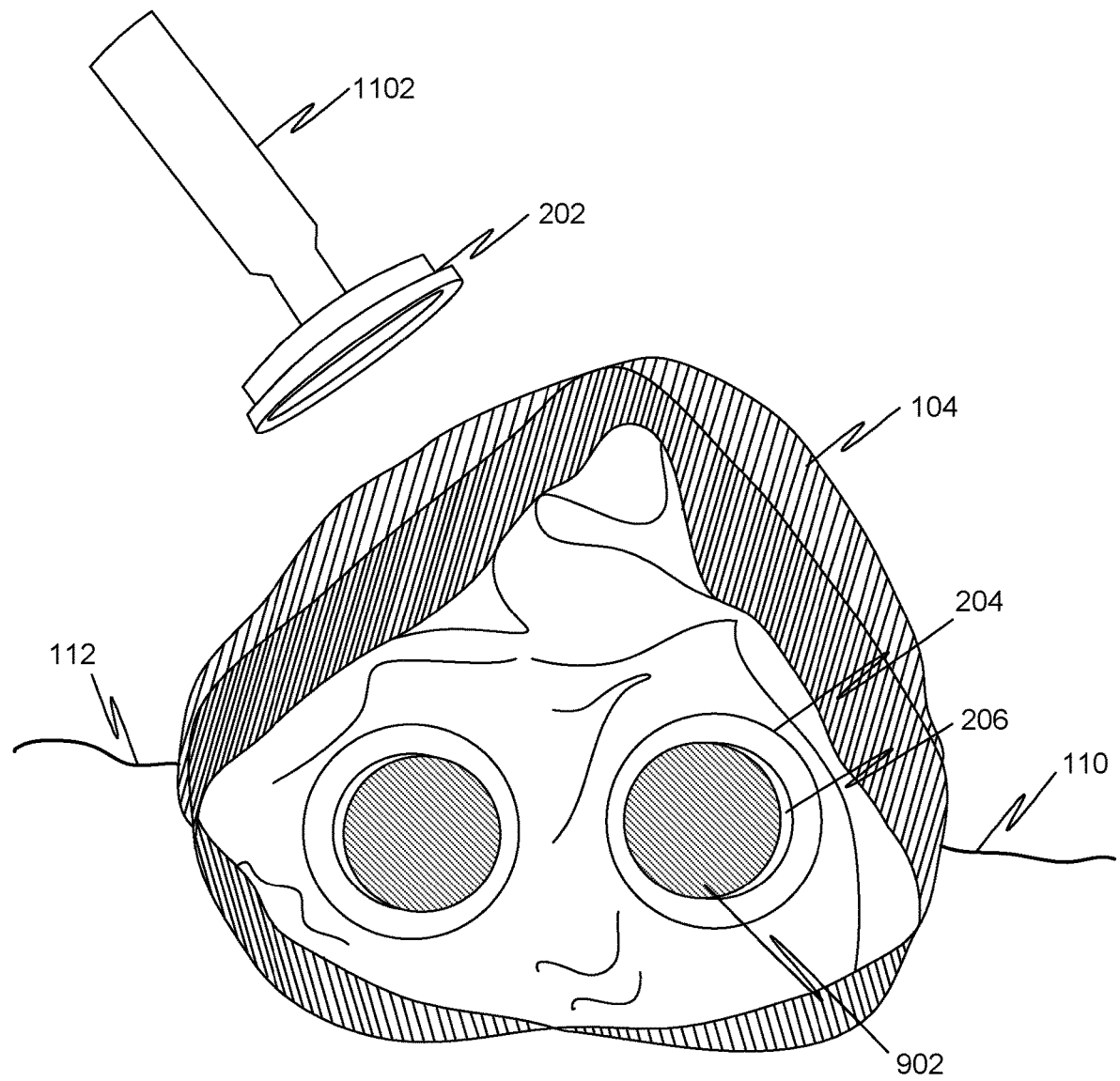
FIG. 16 is a top view of the inside of the headcap for transcranial stimulation, according to an embodiment.

At 1218, the method 1200 includes removing the distributor 208, as shown in FIG. 16. Thereafter, the headcap 104 may be worn by a patient for transcranial stimulation, as shown in FIG. 1. FIG. 16 is a top view of the inside of the headcap 104 for transcranial stimulation.

When the tDCS transcranial direct current stimulator is switched on, stimulation is started. The stimulation current (e.g. 2 mA) may be carried from the stimulator, through the cables 110-112, via the PCB 206 and then through the saline-soaked hydrogel (on the gel pad 902), and into the patient's scalp on the anodal side (typically left), and close the circuit by returning to the stimulator from the cathodal (typically right) side.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A system for facilitating administration of transcranial stimulation, the system comprising:

an electrode comprising:
 a counterpart configured to be attached to a headcap;
 a gel cup configured to be attached to the counterpart, wherein the gel cup comprises a first side configured to be disposed towards a head of a subject, a second side configured to be attached to the counterpoint and an interior space;
 an electrical conductor configured to be disposed within the interior space of the gel cup;
 a gel pad comprising a hydrophilic material, wherein the gel pad is arranged to be in contact with the electrical conductor; and
 a distributor configured to be removably attached to the first side of the gel cup and is removed from the first side of the gel cup prior to the transcranial simulation, wherein the distributor comprises:
at least one inlet an aqueous solution; and
 at least one inlet configured to receive an aqueous solution; and
 a plurality of outlets in a fluid communication with the at least one inlet, wherein the plurality of outlets is configured to direct the aqueous solution towards the gel pad.

2. The system of claim 1, further comprising the headcap configured to be worn over a head portion of a user.

3. The system of claim 1, wherein the counterpart comprises attaching means configured to attach the counterpart to the headcap.

4. The system of claim 1, wherein the electrode further comprises a frame part wherein the first side is attached to the frame part.

5. The system of claim 1, wherein the electrode further comprises:
 a printed circuit board (PCB) configured to be disposed within the interior space of the gel cup, wherein a surface of the PCB comprises the electrical conductor; and
 an electrical cable comprising a first end and a second end, wherein the first end is electrically connected to the electrical conductor, wherein the second end of the cable is configured to be connectable to an output terminal of a transcranial direct current stimulator.

6. The system of claim 1, wherein the distributor comprises a main body and an enclosure attached to the main body to form the fluid communication, wherein the main body comprises the at least one inlet, wherein the enclosure comprises the plurality of outlets.

7. The system of claim 1, wherein the plurality of outlets is evenly arranged over a surface of the distributor, wherein the surface faces the interior space while the distributor is attached to the gel cup.

8. The system of claim 1, wherein a number of the plurality of outlets is in the range of three to ten.

9. The system of claim 1, wherein a first diameter of each outlet is smaller than a second diameter of the inlet.

10. The system of claim 1, wherein the hydrophilic material comprises a superporous hydrogel.

11. A kit for facilitating administration of transcranial stimulation, the kit comprising:
 an electrode comprising:
 a counterpart configured to be attached to a headcap;
 a gel cup configured to be attached to the counterpart, wherein the gel cup comprises a first side configured to be disposed towards a head of a subject, a second side configured to be attached to the counterpart and an interior space;
 an electrical conductor configured to be disposed within the interior space of the gel cup;
 a gel pad comprising a hydrophilic material, wherein the gel pad is arranged to be in contact with the electrical conductor; and
 a distributor configured to be removably attached to the first side of the gel cup and is removed from the first side of the gel cup prior to the transcranial simulation, wherein the distributor comprises:
 at least one inlet configured to receive an aqueous solution;
 a plurality of outlets in a fluid communication with the at least one inlet, wherein the plurality of outlets is configured to direct the aqueous solution towards the gel pad; and
 a container for the aqueous solution, which container is removably connectable to the inlet of the distributor.

12. The kit of claim 11 further comprising the headcap configured to be worn over a head portion of a user.

13. The kit of claim 11, wherein the counterpart comprises an attaching means configured to attach the counterpart to the headcap.

14. The kit of claim 11, wherein the kit further comprises a frame part, wherein the first side is configured to be attached to the frame part.

15. The kit of claim 11, wherein the kit further comprises:
 a printed circuit board (PCB) configured to be disposed within the interior space of the gel cup, wherein a surface of the PCB comprises the electrical conductor; and
 an electrical cable comprising a first end and a second end, wherein the first end is configured to be electrically connectable to the electrical conductor, wherein the second end of the cable is configured to be connectable to an output terminal of a transcranial direct current stimulator.

16. The kit of claim 11, wherein the distributor comprises a main body and an enclosure attachable to the main body to form the fluid communication, wherein the main body comprises the at least one inlet, wherein the enclosure comprises the plurality of outlets.

17. The kit of claim 11, wherein the plurality of outlets is evenly arranged over a surface of the distributor, wherein the surface faces the interior space while the distributor is attached to the gel cup.

18. The kit of claim 11, wherein a first diameter of each outlet is smaller than a second diameter of the inlet.

19. The kit of claim 11, wherein the hydrophilic material comprises a superporous hydrogel.

20. The kit of claim 11, wherein the container comprises a mouth configured to couple with the at least one inlet to facilitate flow of the aqueous solution into the at least one inlet.

* * * * *